(12) United States Patent
Crabtree et al.

(10) Patent No.: US 8,979,733 B2
(45) Date of Patent: Mar. 17, 2015

(54) SYNTHETIC URETHRA WITH CLOSURE DEVICE

(75) Inventors: Tim Crabtree, Plymouth, MN (US);
Nicholas Ellering, Crystal, MN (US);
Allen Gaynor, Coon Rapids, MN (US);
Michael B. Hektner, Minneapolis, MN (US); Steve Knop, Maple Grove, MN (US)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 13/469,105

(22) Filed: May 11, 2012

(65) Prior Publication Data

US 2013/0079587 A1    Mar. 28, 2013

Related U.S. Application Data

(60) Provisional application No. 61/538,864, filed on Sep. 25, 2011.

(30) Foreign Application Priority Data

Sep. 23, 2011    (DK) .................................. 2011 70527

(51) Int. Cl.
*A61F 2/00* (2006.01)
*A61F 2/02* (2006.01)
*A61F 2/04* (2013.01)

(52) U.S. Cl.
CPC ............ *A61F 2/0031* (2013.01); *A61F 2/0036* (2013.01); *A61F 2/004* (2013.01); *A61F 2/04* (2013.01); *A61F 2002/047* (2013.01); *A61F 2250/0013* (2013.01)

USPC ........................................................ 600/31

(58) Field of Classification Search
CPC ...... A61F 2/0031; A61F 2/0036; A61F 2/004; A61F 2/042
USPC .............. 600/29–32; 623/23.64, 23.66–23.68
See application file for complete search history.

(56) References Cited

U.S. PATENT DOCUMENTS

| 5,634,878 | A | * | 6/1997 | Grundei et al. ................ 600/30 |
| 2003/0225311 | A1 | | 12/2003 | Sayet et al. |
| 2007/0249893 | A1 | * | 10/2007 | Krumme ......................... 600/31 |
| 2009/0105814 | A1 | * | 4/2009 | Groothuis et al. ........... 623/2.36 |
| 2010/0222894 | A1 | * | 9/2010 | Forsell ....................... 623/23.71 |

FOREIGN PATENT DOCUMENTS

| DE | 19511998 | 10/1996 |
| EP | 1082946 | 3/2001 |
| JP | 7051304 | 2/1995 |
| JP | 7051305 | 2/1995 |

* cited by examiner

*Primary Examiner* — Christine Matthews
*Assistant Examiner* — Thaddeus Cox
(74) *Attorney, Agent, or Firm* — Coloplast Corp., Coloplast A/S; Nick Baumann (57) ABSTRACT

An incontinence treatment device includes a section of synthetic urethra and a closure device attached to the section of synthetic urethra. The section of synthetic urethra provides a flow diameter and is configured to be spliced into a natural urethra such that the flow diameter is aligned with a lumen of the natural urethra for passage of urine. The closure device is attached to the section of synthetic urethra and operable to coapt the flow diameter to allow a user to impede the passage of urine and be continent.

19 Claims, 10 Drawing Sheets

SYNTHETIC URETHRA WITH CLOSURE DEVICE

BACKGROUND

Devices for treating urinary incontinence include slings, supports, artificial urinary sphincters and other devices that are implanted in a patient's body to support and/or coapt the urethra.

A sling is a device that is surgically implanted under the urethra to support the urethra and inhibit urine from leaking out of the urethra during a provocative event such as coughing or sneezing. Slings are typically implanted through one or more incisions and anatomically secured to supporting tissue (s).

An artificial urinary sphincter is generally provided as an inflatable ring or cylinder that is surgically implanted around a portion of the urethra. Some people become incontinent after having some or the entire prostate removed, which can result in a loss of some or all of the function of the prostatic urinary sphincter. An artificial urinary sphincter implanted around the compromised prostatic urinary sphincter can provide the patient with improved control of urinary function. However, the placement of an artificial urinary sphincter around a section of natural urethra can lead to undesirable erosion of the tissue of the urethra, which has the potential to reduce the efficacy of the artificial sphincter.

Improved incontinence treatment devices would be welcomed by both the patient and the surgical staff.

SUMMARY

One aspect provides an incontinence treatment device including a synthetic urethra and a closure device for the synthetic urethra. The synthetic urethra provides a flow diameter that is configured to be spliced into a natural urethra such that the flow diameter is aligned with a lumen of the natural urethra for passage of urine. The closure device includes a pump communicating between a reservoir and a manifold. The manifold is attached to a wall of the synthetic urethra. The pump is operable to move a liquid from the reservoir to the manifold to displace the wall and substantially close the flow diameter of the synthetic urethra.

One aspect provides an incontinence treatment device including a synthetic urethra and a closure device for the synthetic urethra. The synthetic urethra provides a flow diameter that is configured to be spliced into a natural urethra such that the flow diameter is aligned with a lumen of the natural urethra for passage of urine. The closure device includes a pump communicating between a reservoir and a cuff. The cuff is separate from the synthetic urethra and attachable around an outer circumference of the synthetic urethra. The pump is operable to move a liquid from the reservoir to inflate the cuff, and the inflated cuff is adapted to circumferentially compress and constrict the flow diameter of the synthetic urethra.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

Tissue includes soft tissue, which includes dermal tissue, sub-dermal tissue, ligaments, tendons, or membranes. As employed in this specification, the term "tissue" does not include bone.

In this specification the word "coapt" means to close or to substantially close. To coapt an opening is to bring two surfaces together in close approximation such that the gap between the two surfaces is reduced or eliminated. To coapt a flow diameter means to substantially close the flow diameter to impede the passage of fluid flow through the flow diameter, which when the fluid is urine provides a person with a continent state.

In this specification a synthetic urethra is a urethra that is not the patient's natural urethra. A synthetic urethra is an artificial urethra. A synthetic urethra or a section of synthetic urethra replaces a portion of the patient's natural urethra to provide a flow diameter for urine between the bladder and the distal exit of the urethra. A synthetic urethra is not a catheter that is inserted into a urethra.

Embodiments provide an incontinence treatment device that addresses the issue of erosion of the urethra by providing a section of synthetic urethra and a closure device that is attachable to the section of synthetic urethra. The section of synthetic urethra is configured to be more compliant and more resistant to erosion the natural urethra. The closure device is attachable to the section of synthetic urethra to allow the user to selectively close the flow path through the synthetic urethra to achieve a continent state. The section of synthetic urethra is adapted to be spliced between portions of the natural urethra.

Figure 1:
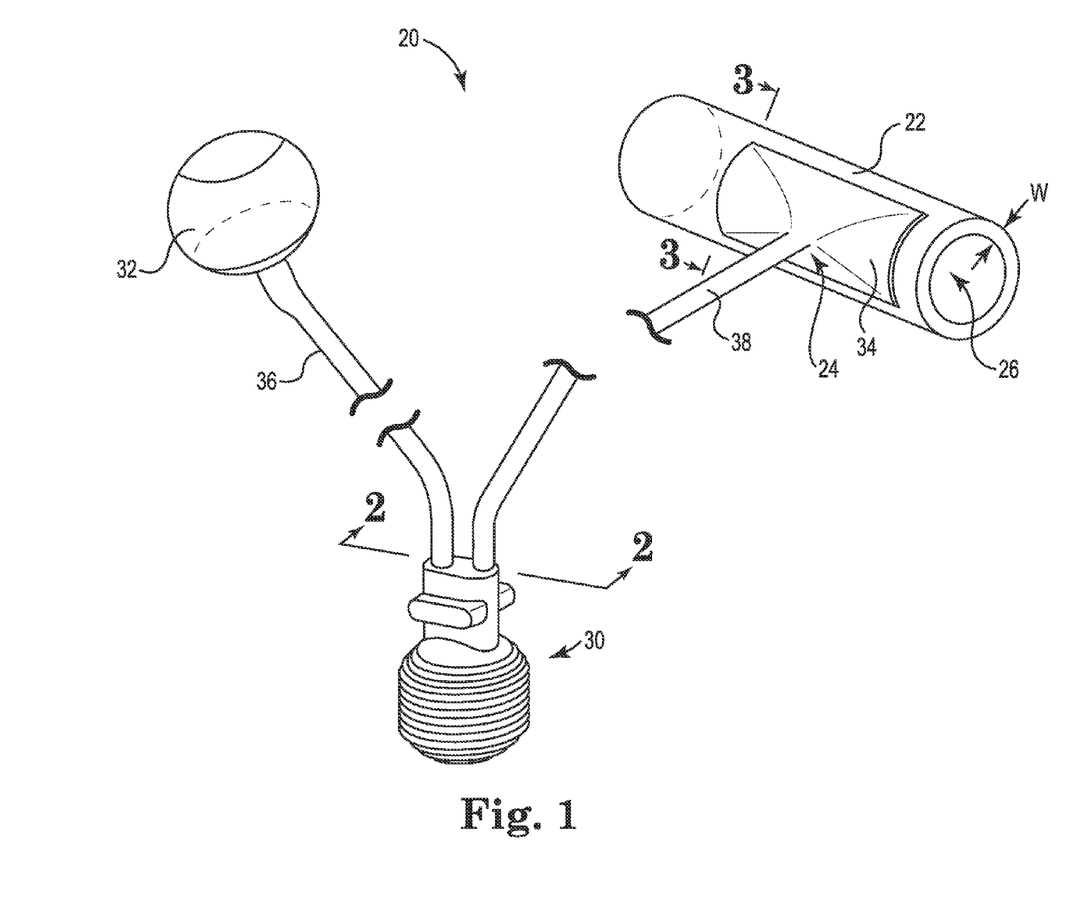
FIG. 1 is a perspective view of one embodiment of an incontinence treatment device including a closure device attached to a synthetic urethra.

FIG. 1 is a perspective view of one embodiment of an incontinence treatment device 20 (device 20). The device 20 includes a section 22 of synthetic urethra and a closure device 24 attached to the section 22 of synthetic urethra. The section 22 of synthetic urethra provides a flow diameter 26 sized to be spliced into a portion of a natural urethra to accommodate urine flow. The closure device 24 is operable to selectively close the flow diameter 26 to provide the user with a continent state.

In one embodiment, the closure device 24 includes a pump 30 that communicates between a reservoir 32 and a manifold 34 that is attached to the section 22 of synthetic urethra. For example, in one embodiment a tube 36 is connected between the reservoir 32 and the pump 30 and a separate tube 38 is connected between the pump 30 and the manifold 34. The tubes 36, 38 generally provide pathways for liquid that is transported through the action of the pump 30 between the reservoir 32 and the manifold 34. The tubes 36, 38 can optionally include quick-connect and quick-disconnect attachment features that allow the surgeon to connect the tubes 36, 38 after implanting the section 22 of synthetic urethra, the pump 30, and the reservoir 32.

The section 22 of synthetic urethra is sized to be spliced between sections of natural urethra and in one embodiment has an outside diameter of between about 2-10 mm, preferably between about 4-8 mm. In one embodiment, the wall thickness W of the section 22 of synthetic urethra is between about 0.25-1 mm. The length of the section 22 of synthetic urethra is based on the anatomy of the user. For a male user the length of the section 22 of synthetic urethra is between about 2-16 cm, and for a female user the length of the section 22 of synthetic urethra is between approximately 1-4 cm. The above dimensions are provided as suitable examples, although one of ordinary skill in the art will recognize that other dimensions are acceptable based on the size of the anatomy of the end-user.

In one embodiment, the section 22 of synthetic urethra is sized to be spliced between sections of a natural prostatic urethra, between sections of a natural membranous urethra, between sections of a natural bulbar urethra, or between sections of a natural penile urethra, or between two of these urethral sections.

The section 22 of synthetic urethra is suitably fabricated from natural materials or polymer materials. For example, in one embodiment the section 22 of synthetic urethra is fabricated from autograft material (the patient's own tissue), allograft material (tissue from a cadaver), xenograft material (tissue from another species), decellularized tissue such as decellularized allograft tissue, or synthetic materials such as rubber, silicone, thermoplastic polymers, thermoset polymers, or blends or copolymers of suitable polymers.

Figure 2:
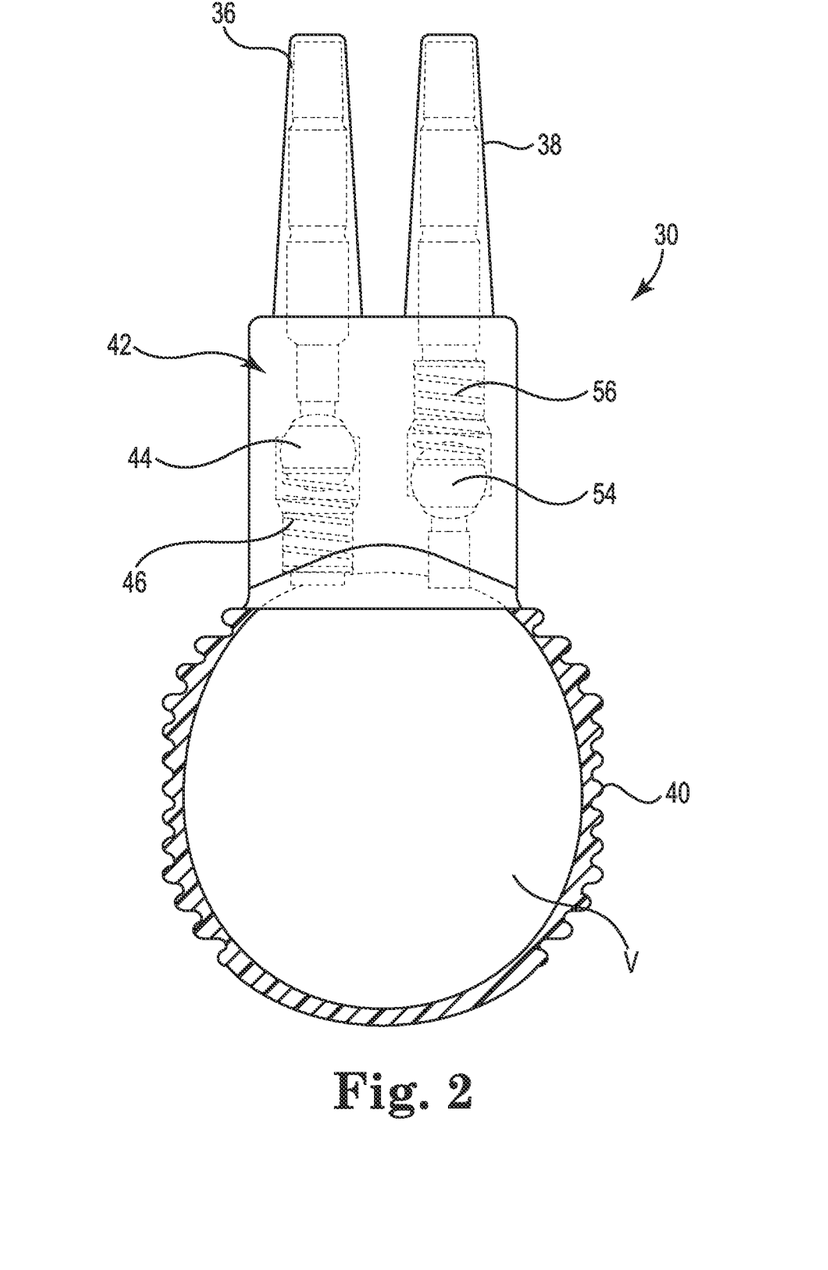
FIG. 2 is a cross-sectional view of a pump of the closure device illustrated in FIG. 1.

FIG. 2 is a cross-sectional view of one embodiment of the pump 30. The pump 30 includes a bulb 40 having with a bulb volume V and a valve assembly 42 communicating with the tubes 36, 38. In one embodiment, the valve assembly 42 includes an inlet valve 44 biased by a spring 46 and an outlet valve 54 biased by a spring 56. The bulb 40 is compressible to eject a portion of the bulb volume V past the outlet valve 54 and through the tube 38 to the manifold 34 (FIG. 1). The compression of the bulb 40 creates a vacuum that sucks or siphons fluid through the tube 36 and across the inlet valve 44 into the expanding bulb 40, which configures the bulb 40 to again eject the fluid from the bulb through the tube 38 to the manifold 34. The valve assembly 42 is illustrated with ball valves 44, 54, although one of ordinary skill in the art will understand that other valves configured to allow liquid to be drawn from the reservoir 32 and ejected to the manifold 34 are also acceptable.

Figure 3A:
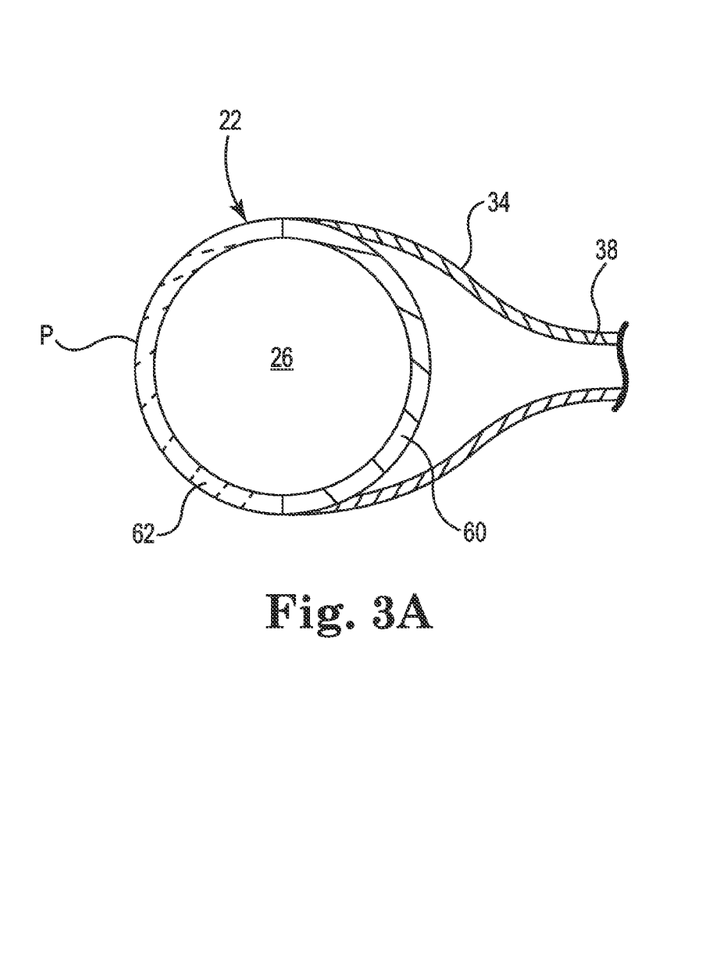
FIG. 3A is a cross-sectional view of the incontinence treatment device illustrated in FIG. 1 showing an open flow diameter through the synthetic urethra sized for the passage of urine.
Figure 3B:
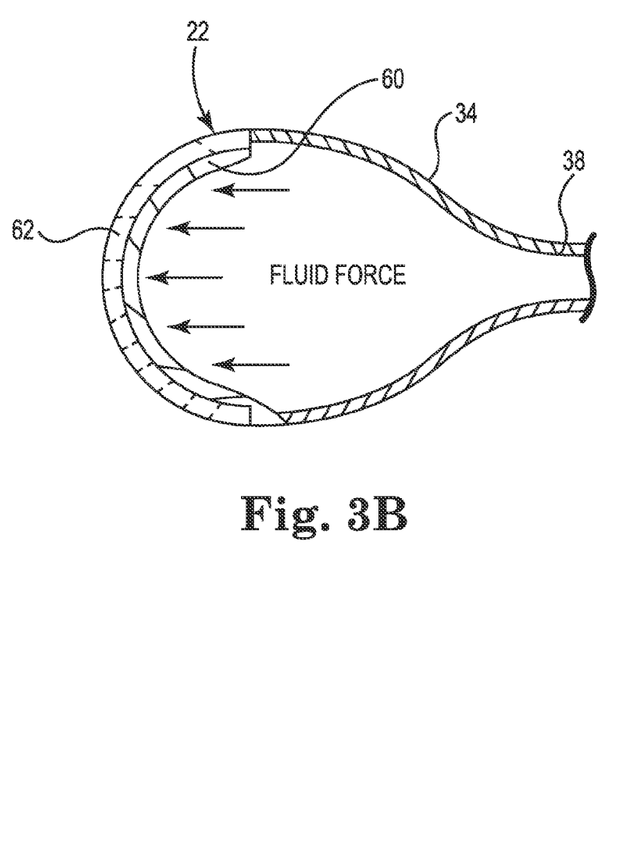
FIG. 3B is a cross-sectional view of the incontinence treatment device illustrated in FIG. 1 showing a coapted flow diameter of the synthetic urethra that impedes the passage of urine to provide the user with a continent state.

FIG. 3A is a cross-sectional view of the manifold 34 attached to an exterior wall of the section 22 of synthetic urethra with the flow diameter 26 in an open position. FIG. 3B is a cross-sectional view of liquid filling the manifold 34 to close the flow diameter 26.

In one embodiment, the section 22 of synthetic urethra is provided as a tubular segment having an outer perimeter P that is provided by a first portion 60 attached to a second portion 62, where the first portion 60 is more flexible than the second portion 62. In this regard, the tubular section 22 of synthetic urethra has a first material property in the first portion 60 that is different than a material property of the second portion 62. For example, the first portion 60 is supplied with a lower durometer material or a more elastic material than the second portion 62. In this manner, the first portion 60 is more easily deformed than the second portion 62 (e.g., the first portion 60 stretches more than the second portion 62) and will respond to a greater extent for a given force is applied to the section 22 of synthetic urethra. In one embodiment, the manifold 34 extends around less than about one-half of the perimeter P of the section 22 of the synthetic urethra. In one embodiment, the manifold 34 extends around approximately one-half of the perimeter P of the section 22 of the synthetic urethra.

In one embodiment, the first portion 60 is fabricated from a rubber having a durometer of between about 20-40 Shore A and the second portion 62 is fabricated from a rubber having a durometer of between about 40-60 Shore A. It is desirable that the manifold 34 is more rigid or firmer than the section 22 of synthetic urethra. In one embodiment, the manifold 34 is fabricated from a rubber or polymer material having a hardness of about 45-70 Shore A such that it is more rigid and less flexible than the section 22 of synthetic urethra.

FIG. 3B illustrates a fluid force acting on the first portion 60 of the tubular section 22 of synthetic urethra. The fluid force presses against the first portion 60 and expands or deforms the first portion 60 inwardly into contact with the second portion 62. In this manner, the pump 30 operates to move liquid from the reservoir 32 to the manifold 34 to move a wall of the first portion 60 of synthetic urethra inward to substantially close the flow diameter 26 to the passage of urine, which coapts or closes the section 22 of synthetic urethra to provide the user with a continent state.

With additional reference to FIG. 1, in one embodiment the fluid force is provided by the pump 30 moving a liquid such as saline from the reservoir 32 into the manifold 34. Alternatively, the fluid force is provided by the pump 30 moving a gas such as air from the reservoir 32 to the manifold 34.

The manifold 34 and the section 22 of synthetic urethra are configured to function over many cycles in a lifetime of use. In one embodiment, the section 22 of synthetic urethra is attached to the manifold 34 such that the section 22 does not slip when the manifold 34 compresses the section 22. The section 22 of synthetic urethra is fabricated to have a response to deformation such that erosion of the synthetic urethra during use is substantially eliminated. In contrast, when an artificial urinary sphincter is placed over a section of natural urethra the natural urethra will tend to erode and become damaged. The manifold 34 of the closure device 24 cooperates with the section 22 of synthetic urethra to reduce or eliminate erosion in the section 22 of synthetic urethra.

Figure 3C:
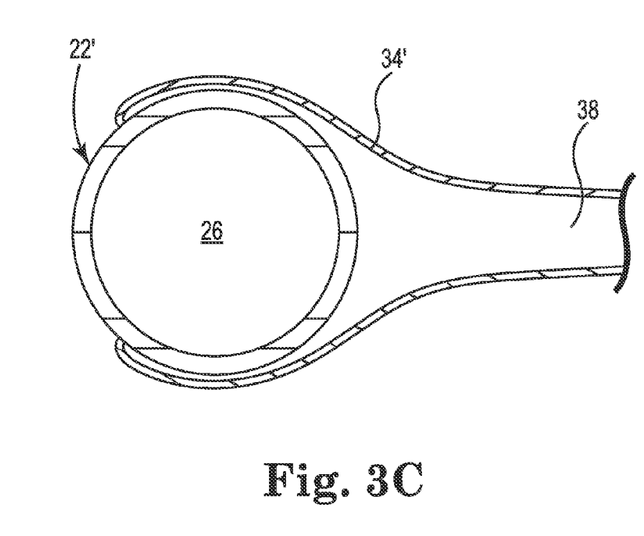
FIG. 3C is a cross-sectional view of one embodiment of a synthetic urethra having an open flow diameter for the passage of urine.
Figure 3D:
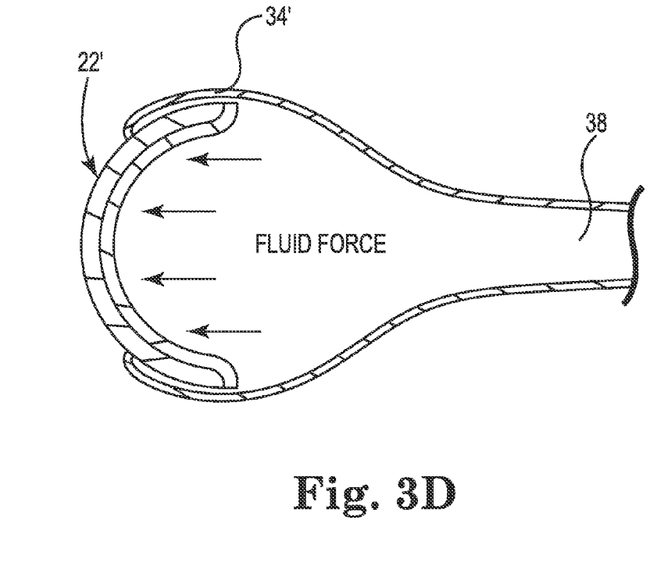
FIG. 3D is a cross-sectional view of the synthetic urethra illustrated in FIG. 3C with a coapted flow diameter that impedes the passage of urine to provide the user with a continent state.

FIG. 3C is a cross-sectional view of a manifold 34' attached to a section 22' of synthetic urethra with the flow diameter 26 in an open position, and FIG. 3D is a cross-sectional view of liquid filling the manifold 34' to close the flow diameter 26.

In one embodiment, the section 22' of synthetic urethra has substantially uniform properties throughout its cross-section and the manifold 34' is attached around most (more than one-half) of the outer perimeter P of the section 22' of synthetic urethra. In this regard, the portions of the wall of the section 22' are equally flexible and elastic and it is desirable to compress a sufficient radial amount of the wall of the section 22' to ensure that the flow diameter 26 can be closed.

FIG. 3D is a cross-sectional view illustrating a fluid force pressing against one wall of the section 22' of synthetic urethra to force the wall to close against an opposing wall of the section 22' synthetic urethra to close the flow diameter 26.

Figure 4:
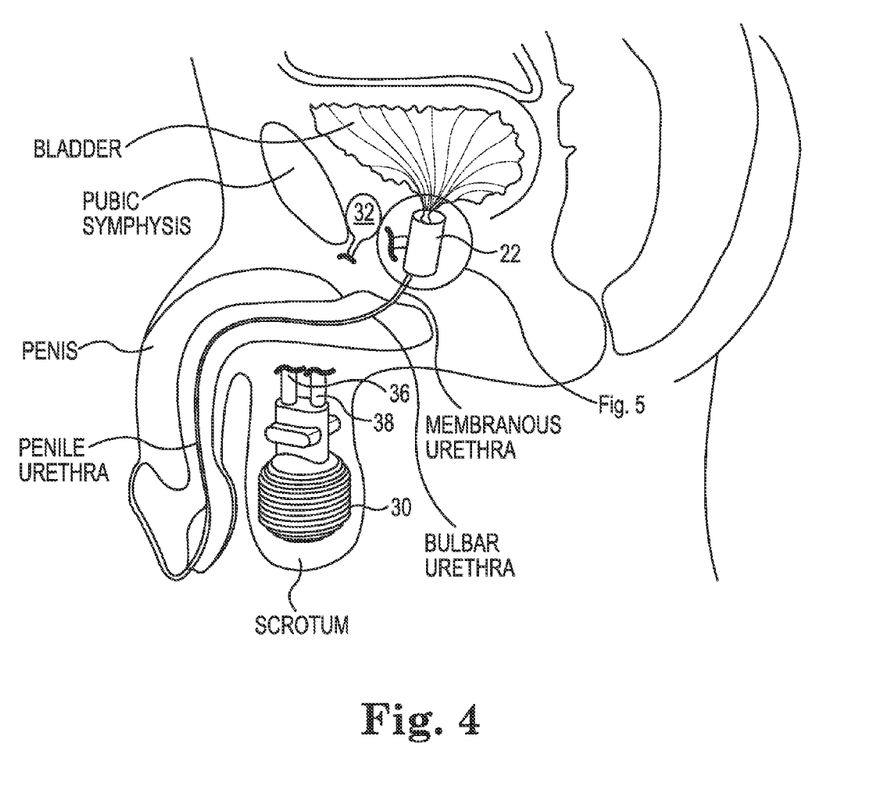
FIG. 4 is a schematic view of the incontinence treatment device illustrated in FIG. 1 implanted in a male user.

FIG. 4 is a schematic view of the incontinence treatment device 20 implanted in a male user. The pump 30 is implanted in the scrotum and communicates between the reservoir 32 and the manifold 34 that is attached to the section 22 of synthetic urethra. The section 22 of synthetic urethra is placed between portions of the natural urethra, for example in a location of the prostatic urethra descending from the bladder. The reservoir 32 is implanted within the patient, for example in the space of Retzius posterior to the pubic symphysis, or alternatively, in a space that is anterior the pubic symphysis.

Figure 5:
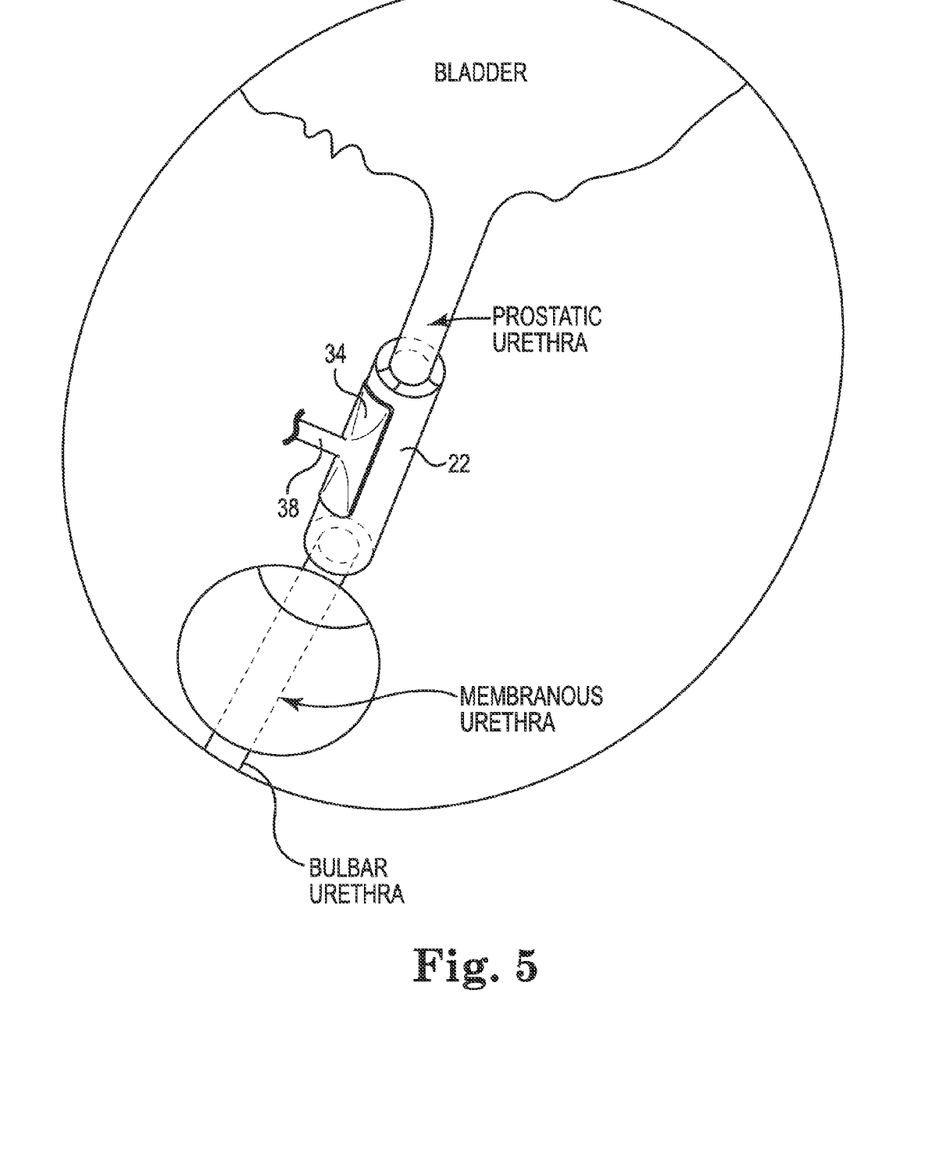
FIG. 5 is a perspective view of the synthetic urethra of the incontinence treatment device illustrated in FIG. 4 spliced between the prostatic urethra and the membranous urethra.

FIG. 5 is a perspective view of the section 22 of synthetic urethra that is spliced between portions of the natural urethra. In one embodiment, the section 22 of synthetic urethra is spliced between the prostatic urethra and the membranous urethra, for example after removal of the prostate gland. The section 22 of synthetic urethra may be suitably spliced to the natural urethra through the use of micro-suturing, welding, adhesive attachment, through the use of bio-adhesive attachment, or through tissue in-growth between the natural urethra and the synthetic urethra.

The section 22 of synthetic urethra is configured to replace a section of damaged urethra, for example as sometimes occurs when the prostate is removed. In other embodiments, the section 22 of synthetic urethra is spliced distal to the membranous urethra, for example in a location of the bulbar urethra, or the section 22 of synthetic urethra is spliced into the pendulous urethra. In one embodiment, a length of the section 22 of synthetic urethra is configured to replace substantially all of the male urethra and has a length of about 20 cm.

Specific aspects of one suitable surgical procedure for placement of the device 20 are described in the following paragraphs. The patient is typically placed in a dorsal lithotomy position with the legs positioned at about 90 degrees and held in place by stirrups. The patient is catheterized, for example with a 14 French catheter to drain the bladder. The surgeon may elect to leave the catheter in place within the urethra until the urethra is severed for placement of the synthetic urethra 22. The surgeon makes a vertical perineal incision in the midline and dissects tissue to eventually isolate the ventral bulbous urethra and the prostatic urethra. The surgeon will subsequently expose the bulbospongiosus muscle and dissect further to expose the natural urethra(s).

In one example, the prostate has been removed and the surgeon dissects down to expose the urethra posterior the bulbous urethra. A portion of the prostatic urethra is appropriately dissected, and at the surgeon's preference, a portion of the prostatic urethra is removed to make place for the synthetic urethra 22. One end of the synthetic urethra is suitably attached to an exposed end the prostatic urethra, for example by micro-suturing or another suitable attachment method that provides a leak resistant attachment of the synthetic urethra 22 to the prostatic urethra. Similarly, an opposing end of the synthetic urethra 22 is attached to an opposing end of the severed prostatic urethra and the flow diameter of the synthetic urethra 22 is aligned with a lumen of the natural urethra.

With additional reference to FIG. 1, the pump 30 is implanted within the scrotum and reservoir 32 is implanted within the abdomen, for example in the space of Retzius. The reservoir 32 is filled with a liquid and attached to the pump 30. The pump 30 is attached to synthetic urethra 22 by the tube 38 and the pump 30 is attached to the reservoir 32 by the tube 36. The surgeon evaluates the function of the pump 30 by moving a liquid from the reservoir 32 into the manifold 34 to coapt the synthetic urethra 22.

The surgical site is closed. The patient is typically catheterized for the duration of the healing process, after which the device 20 is ready for use.

Figure 6:
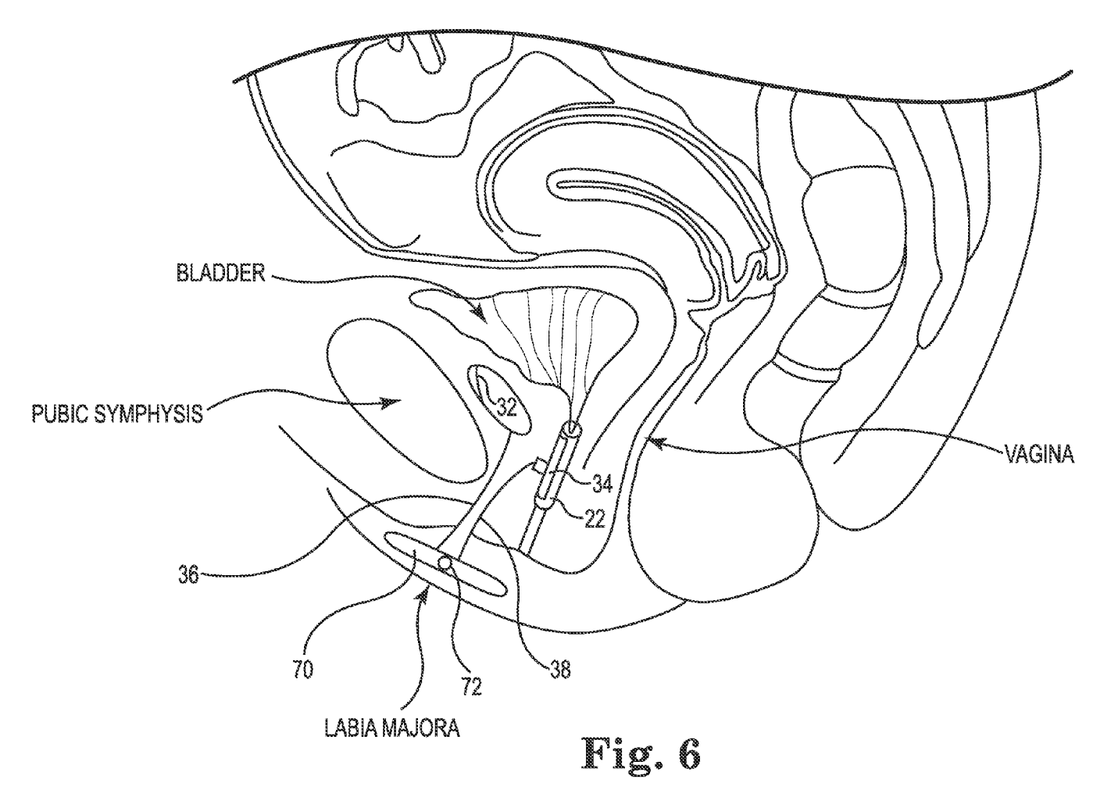
FIG. 6 is a perspective view of one embodiment of a synthetic urethra of an incontinence treatment device as illustrated in FIG. 1 spliced between sections of a natural urethra of a female.

FIG. 6 is a schematic view of the section 22 of synthetic urethra implanted in a female. There urethra of the female is substantially shorter than the urethra of the male and has a length of between about 2-4 cm. With this in mind, the section 22 of synthetic urethra is sized to replace a portion or all of the urethra of the female user and is implanted distal the bladder. In one embodiment, the section 22 synthetic urethra is spliced into the natural urethra of the female user between the trigon of the exit of the bladder and a distal exit of the urethra.

The reservoir 32 is implanted in a suitable location, for example posterior the pubic symphysis. The pump is likewise implanted in a suitable location of the female anatomy, and in one embodiment is sized to be implanted in the labia majora. With this in mind, one suitable pump 70 is provided for implantation into the labia having a length that is greater than its with and includes a valve assembly 72 that operates in a manner similar to the valve assembly 42 described above.

Figure 7:
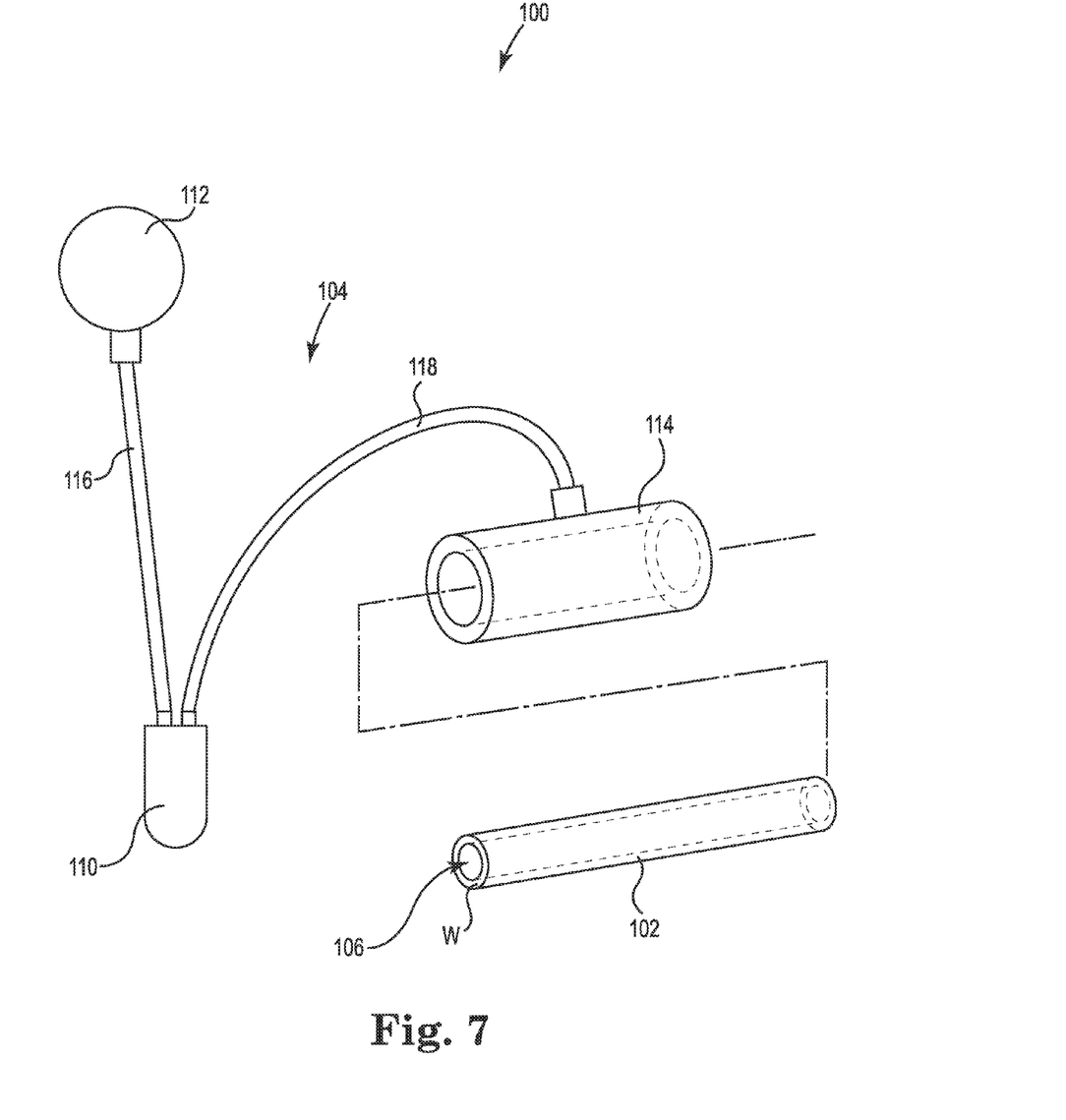
FIG. 7 is a perspective view of one embodiment of an incontinence treatment device including an artificial urinary sphincter closure device attachable to a section of synthetic urethra.

FIG. 7 is a perspective view of one embodiment of an incontinence treatment device 100 (device 100). The device 100 includes a section 102 of synthetic urethra and a closure device 104 that is provided to close a flow diameter 106 in the section 102 of synthetic urethra.

In one embodiment, the closure device 104 is provided as an artificial urinary sphincter 104 and includes a pump 110 connected between a reservoir 112 and an inflatable cuff 114. For example, the pump 110 is connected to the reservoir 112 by a tube 116 and is connected to the cuff 114 by a separate tube 118. The pump 110 is configured to draw a fluid from the reservoir 112 and use the fluid to inflate the cuff 114. In one embodiment, the fluid is liquid and the pump 110 includes a valve assembly similar to the valve assembly 42 described above. In one embodiment, the fluid is a gas and the pump 110 is an electronic pump configured to compress the gas and use the compressed gas to inflate the cuff 114. In any regard, the cuff 114 is configured to inflate and compress a wall W of the section 102 of synthetic urethra to close the flow diameter 106 and provide the user with a continent state.

In one embodiment, the section 102 of synthetic urethra is provided separately from the cuff 114. In one embodiment, the cuff 114 is attached to the synthetic urethra 102, and the synthetic urethra 102 and the cuff 114 are fabricated as a single, monolithic integral unit.

The closure device 104 and the section 102 of synthetic urethra are configured to function over many cycles in a lifetime of use. In one embodiment, the section 102 of synthetic urethra and the closure device 104 are fabricated to have approximately equal response to deformation such that erosion of the synthetic urethra during use is substantially eliminated. In contrast, when an artificial urinary sphincter (AUS) is placed over a section of natural urethra, the natural urethra will tend to erode and become damaged because the AUS is more durable than the natural urethra. The closure device 104 cooperates with the section 102 of synthetic urethra to reduce or eliminate erosion in the synthetic urethra.

Figure 8:
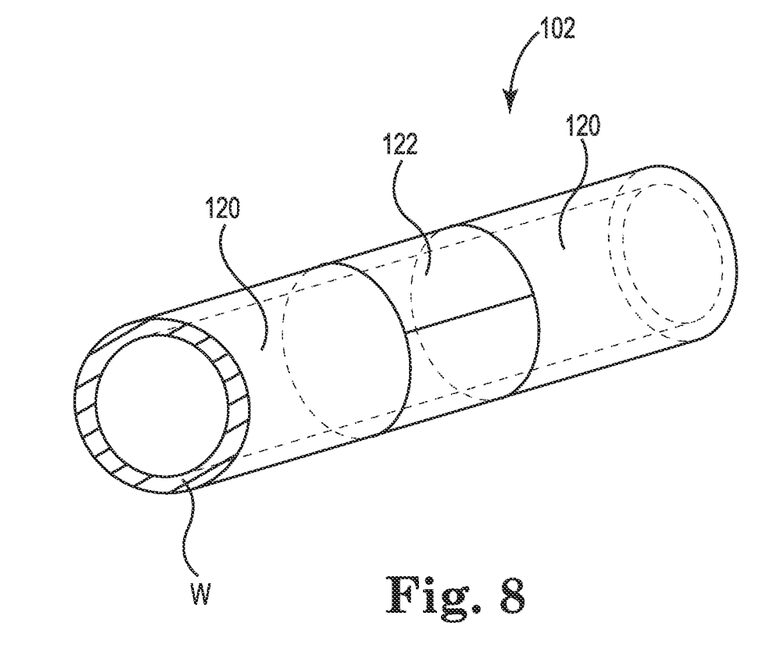
FIG. 8 is a perspective view of one embodiment of the section of synthetic urethra illustrated in FIG. 7.

FIG. 8 is a perspective view of the section 102 of synthetic urethra. In one embodiment, the section 102 of synthetic urethra includes at least a portion that is more flexible or more elastic than the remaining portion of the section 102 of synthetic urethra. For example, in one embodiment the section 102 of synthetic urethra is provided as tube having an annular ring with a first portion 122 that is more flexible than a remaining portion 120 of the tube. In this manner, the first portion 122 that is more flexible is more easily deformed and is configured to be activated with a lower pressure delivered from the pump 110 (FIG. 7).

Figure 9:
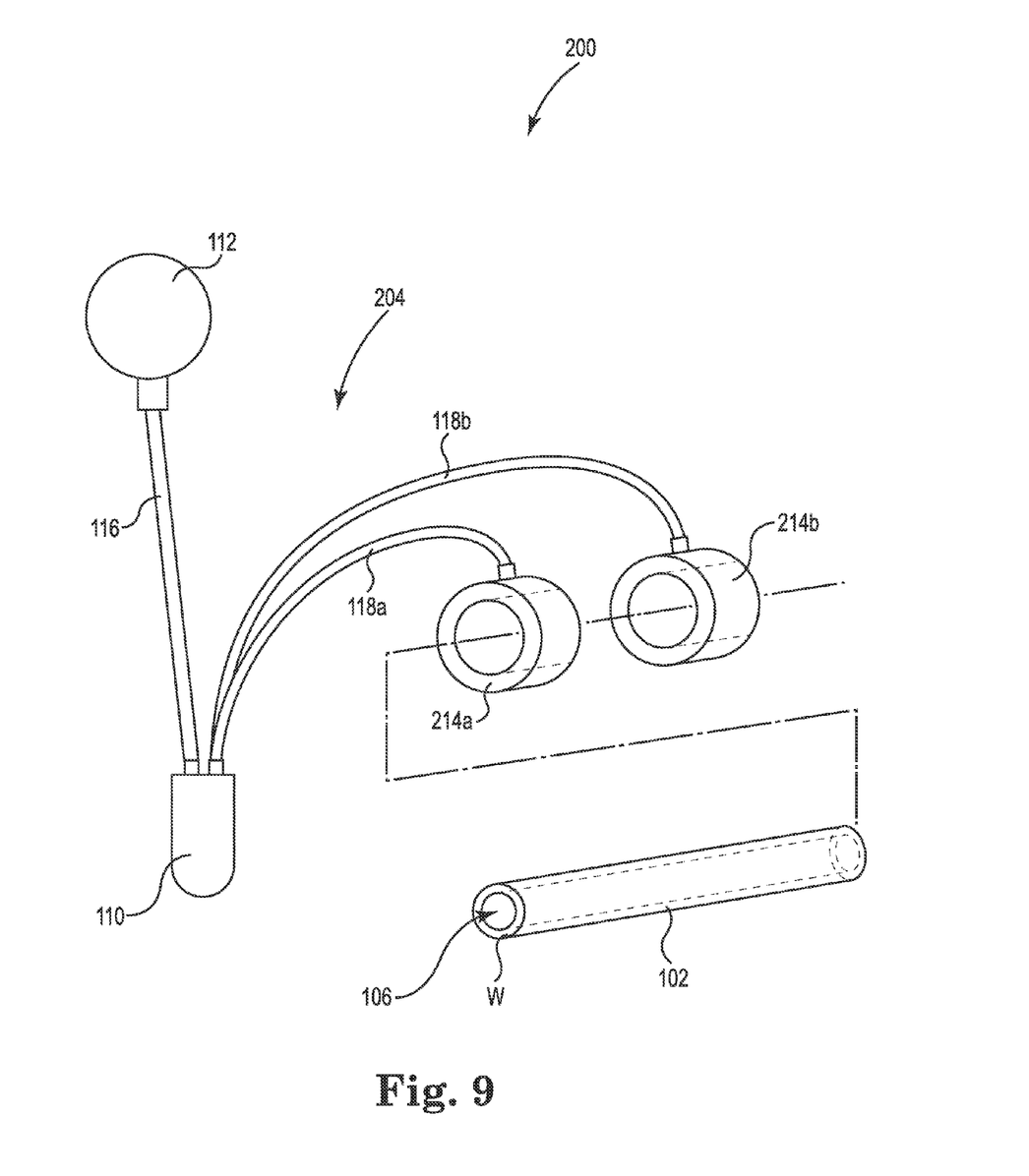
FIG. 9 is a perspective view of one embodiment of an incontinence treatment device including a pair of artificial urinary sphincter closure devices attachable to a section of synthetic urethra.

FIG. 9 is a perspective view of one embodiment of an incontinence treatment device 200 (device 200). The device 200 includes the section 102 of synthetic urethra described above and a closure device 204 that is provided to close the flow diameter 106 in the section 102 of synthetic urethra.

In one embodiment, the closure device 204 is provided with the pump 110 that is connected between the reservoir 112 and a pair of inflatable cuffs 214a, 214b. For example, the pump 110 is connected to the reservoir 112 by the tube 116 and the pump 110 is connected to the first cuff 214a by a first tube 118a and to the second cuff 214b by a second tube 118b. The pump 110 is configured to draw a fluid from the reservoir 112 and use the fluid to inflate the both of the cuffs 214a, 214b to ensure that a sufficient compression is delivered to the section 102 of synthetic urethra to close the flow diameter 106.

The above-described closure devices 24, 104, 204 provide means for coapting the flow diameter of a synthetic urethra to allow a user to selectively impede the passage of urine through the synthetic urethra to control continence.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of medical devices as discussed herein. Therefore, it is intended that this invention be limited only by the claims and the equivalents thereof.

What is claimed is:

1. An incontinence treatment device comprising:
    a section of synthetic urethra that includes a circumferential wall defining an inner surface, an outer surface, and a length, the circumferential wall providing a flow diameter and being configured to be spliced into a natural urethra such that the flow diameter is aligned with a lumen of the natural urethra for passage of urine; and a closure device including a manifold having a manifold wall being positioned external to and attached directly to the outer surface of the circumferential wall of the section of synthetic urethra such that the manifold wall extends about less than an entire circumference of the synthetic urethra, wherein the manifold wall and a displaceable portion of the circumferential wall combine to define a manifold space;
    a fluid reservoir for maintaining a liquid; and
    a pump communicating between the fluid reservoir and the manifold space and operable to move the liquid from the reservoir to the manifold space to pressurize the manifold space and displace the displaceable portion of the circumferential wall to coapt the flow diameter to allow a user to impede the passage of urine and be continent.

2. The incontinence treatment device of claim 1, wherein the section of synthetic urethra has an outside circumference and the closure device is attached to the section of synthetic urethra along only approximately half or less of the outside circumference.

3. The incontinence treatment device of claim 1, wherein the section of synthetic urethra is a tube having a perimeter provided by a first portion attached to a second portion, and the first portion of the tube is more flexible than the second portion of the tube.

4. The incontinence treatment device of claim 3, wherein the closure device is attached to the more flexible first portion of the tube.

5. The incontinence treatment device of claim 1, wherein the section of synthetic urethra is fabricated from one of a polymer and a decellularized tissue.

6. The incontinence treatment device of claim 1, wherein the section of synthetic urethra is sized to be spliced into one of a section of a natural prostatic urethra, a natural membranous urethra, a natural bulbar urethra, and a natural penile urethra.

7. The incontinence treatment device of claim 1, wherein the circumferential wall is substantially smooth.

8. An incontinence treatment device comprising:
    a synthetic urethra including a circumferential wall having an outer surface and an inner surface, the inner surface defining a lumen having a flow diameter, the synthetic urethra being configured to be spliced into a natural urethra such that the flow diameter is aligned with a lumen of the natural urethra for passage of urine;
    a closure device comprising a manifold wall attached directly to the outer surface of the circumferential wall of the synthetic urethra along less than an entire circumference of the outer surface of the synthetic urethra, the manifold wall and the outer surface combining to define a manifold space; and
    a pump for communicating between a fluid reservoir and the manifold space, wherein the pump is operable to move a liquid from the fluid reservoir to the manifold space to displace the circumferential wall and substantially close the flow diameter of the synthetic urethra.

9. The incontinence treatment device of claim 8, wherein the manifold wall is only attached along approximately half or less of an outer circumference of the circumferential wall of the synthetic urethra.

10. The incontinence treatment device of claim 9, wherein the circumferential wall has a first section and a second section that is more flexible than the first section such that the second section is expandable inward toward the first section.

11. The incontinence treatment device of claim 10, wherein the closure device is attached to the flexible second section of synthetic urethra.

12. The incontinence treatment device of claim 8, wherein the synthetic urethra and the manifold wall are fabricated to have approximately equal response to deformation such that erosion of the synthetic urethra during use is substantially eliminated.

13. An incontinence treatment device comprising:
   a section of synthetic urethra providing a flow diameter and configured to be spliced into a natural urethra such that the flow diameter is aligned with a lumen of the natural urethra for passage of urine, the synthetic urethra including an outer wall; and
   means for coapting the flow diameter to allow a user to selectively impede the passage of urine through the synthetic urethra to control continence, wherein the means for coapting the flow diameter including a manifold wall that is positioned external to the outer wall of the synthetic urethra and is attached directly to the outer wall of the synthetic urethra only partially about the outer wall of the synthetic urethra, the manifold wall and a displaceable portion of the outer wall combining to define a manifold space for receiving pressurized fluid from a fluid reservoir such that the displaceable portion of the outer wall is displaceable by the pressurized fluid to close the flow diameter.

14. The incontinence treatment device of claim 13, wherein the section of synthetic urethra is a tube having a perimeter provided by a first portion attached to a second portion, and the first portion of the tube is more flexible than the second portion of the tube.

15. The incontinence treatment device of claim 13, wherein the section of synthetic urethra is sized to be spliced into one of a section of a natural prostatic urethra, a natural membranous urethra, a natural bulbar urethra, and a natural penile urethra.

16. The incontinence treatment device of claim 13, wherein the means for coapting the flow diameter is only attached along approximately half or less of the outer wall of the synthetic urethra.

17. An incontinence treatment device comprising:
   a synthetic urethra including a circumferential wall having an outer surface and an inner surface defining a flow diameter that is configured to be spliced into a natural urethra such that the flow diameter is aligned with a lumen of the natural urethra for passage of urine; and
   a closure system comprising a pump communicating between a reservoir and a manifold space, the manifold space being defined by a manifold wall and a displaceable portion of the circumferential wall, the manifold wall being positioned external to the outer surface of the synthetic urethra and attached on the outer surface of the synthetic urethra only partially about the synthetic urethra such that upon alignment of the natural urethra with the synthetic urethra, the natural urethra is not engaged by the manifold wall and the pump is operable to move a liquid from the reservoir to the manifold space to displace the inner surface of the synthetic urethra and substantially close the flow diameter of the synthetic urethra; wherein the synthetic urethra and the manifold wall are fabricated to have approximately equal response to deformation such that erosion of the synthetic urethra during use is substantially eliminated.

18. The incontinence treatment device of claim 17, wherein the manifold wall is only attached along approximately half or less of the outer surface of the synthetic urethra.

19. An incontinence treatment device comprising:
   a synthetic urethra including a circumferential wall having an outer surface and an inner surface, the inner surface defining a lumen having a flow diameter, the synthetic urethra being configured to be spliced into a natural urethra such that the flow diameter is aligned with a lumen of the natural urethra for passage of urine;
   a manifold wall positioned externally to and attached directly to the outer surface of the circumferential wall of the synthetic urethra such that the manifold wall extends about less than an entire circumference of the synthetic urethra, the manifold wall and a displaceable portion of the circumferential wall combining to define a manifold space;
   a fluid reservoir for maintaining a liquid; and
   a pump communicating between the fluid reservoir and the manifold space and operable to move the liquid from the reservoir to the manifold space to pressurize the manifold space and displace the displaceable portion of the circumferential wall to coapt the flow diameter.

* * * * *